United States Patent [19]
Nitsas

[11] Patent Number: 6,106,838
[45] Date of Patent: Aug. 22, 2000

[54] PHARMACEUTICAL COMPOSITIONS CONTAINING HERBAL-BASED ACTIVE INGREDIENTS; METHODS FOR PREPARING SAME AND USES OF SAME FOR MEDICAL AND VETERINARY PURPOSES

[76] Inventor: Fotios A. Nitsas, Kristoni, GR-611 00 Kilkis, Greece

[21] Appl. No.: 08/981,946

[22] PCT Filed: Jun. 27, 1996

[86] PCT No.: PCT/GR96/00016

§ 371 Date: Dec. 29, 1997

§ 102(e) Date: Dec. 29, 1997

[87] PCT Pub. No.: WO97/01348

PCT Pub. Date: Jan. 16, 1997

[30] Foreign Application Priority Data

Jun. 29, 1995 [GR] Greece ................................. 950100249

[51] Int. Cl.[7] ........................... A61K 35/78; A01N 25/00; A23L 1/222
[52] U.S. Cl. ........................ 424/195.1; 424/404; 424/405; 424/439; 426/2; 426/53; 426/489; 426/542; 426/651; 426/655; 514/885
[58] Field of Search ................................ 424/195.1, 439, 424/404, 405; 426/489, 651, 542, 2, 655, 53; 514/885

[56] References Cited

PUBLICATIONS

Baser et al. J. Essent. Oil Res. vol. 5 (6), pp. 616–623 (abstract enclosed), 1993.
Lagouri et al. Zeitschrift fuer Leensmittel Unter. und Fors. vol. 197 (1), pp. 20–23, 1993.
Akguel et al. Nahrung. vol. 32 (2), pp. 201–203, 1988.
Sarer et al. Planta Med. vol. 46 (4), pp. 236–239 (abstract enclosed), 1982.
Van den Broucke et al. Planta Med. vol. 38 (3), pp. 264–266 (abstract enclosed), 1980.
Assaf et al. Planta Med. vol. 53 (4), pp. 343–345 (abstract enclosed), 1987.

*Primary Examiner*—Leon B. Lankford, Jr.
*Assistant Examiner*—Christopher R. Tate
*Attorney, Agent, or Firm*—St. Onge Steward Johnston & Reens LLC

[57] ABSTRACT

Methods for treating and preventing coccidiosis in poultry, and inflammation, infection, and diarrhea in mammals are provided utilizing an antimicrobial pharmaceutical composition comprising an herbal essential oil which contains thymol and carvacrol as its main ingredients. The essential oil is preferably obtained from the genus Origanum, especially *Origanum vulgare* ssp. *hirtum*.

12 Claims, No Drawings

PHARMACEUTICAL COMPOSITIONS CONTAINING HERBAL-BASED ACTIVE INGREDIENTS; METHODS FOR PREPARING SAME AND USES OF SAME FOR MEDICAL AND VETERINARY PURPOSES

FIELD OF THE INVENTION

The present invention relates to the preparation of various forms of pharmaceuticals for medical and veterinary uses, said pharmaceuticals comprising as active ingredients special herbal essences, capable of substituting antibiotics and sulphamide based drugs, due to their important activity against germs causing inflammations, infections and diarrhoea in humans and animals.

DESCRIPTION OF RELATED ART

The presently used methods for treatment of inflammations, infections and diarrhoea in humans and animals rely on the use of pharmaceuticals that contain antibiotics and sulphamides. It is known that these pharmaceuticals are often the cause of severe short and long term side effects, for example the accumulation of bioresidues. In addition, microorganisms that are to be combatted by these pharmaceuticals develop with time a resistance to these drugs, thus reducing the efficiency of the treatment.

This is because the living organism of humans or animals is incapable of fully assimilating or rejecting these chemicals, resulting in accumulation of chemical in the organism and causing serious side effects exemplified by hereditary changes or sensitivity to microorganisms against which these chemicals had been used.

It is to be noted that animals are more subjected to frequent use of antibiotics than humans. It is known that antibiotics against infections and inflammations are regularly administered on a daily basis to livestock by enrichment of livestock foodstuffs (poultry dough) to prevent diarrhoea and coccidiosis.

This is because in their effort to preserve their livestock capital from infectious, inflammatory and diarroeic diseases, stock-farmers inconsiderately resort to frequent use of these pharmaceuticals and this practice, although helpful in the treatment of said diseases, results in consumer products being charged with elevated quantities of antibiotics.

The situation in humans is to a lesser extent but equally alarming, as many deaths are reported that are caused by prolonged treatment with antibiotics.

BACKGROUND OF THE INVENTION

The present invention refers to compositions containing essential oils that are as effective against inflammations, infections and diarrhoea as antibiotics and sulphamides, but differ essentially from the latter (and this is due to the herbal origin of these essential oils) in that they are fully assimilable or rejectable by the living organism, thus avoiding bioresidues and side effects.

These substances originating from herbal essences, in admixture with inert substances according to methods that are described below, constitute the essential ingredients of pharmaceutical compositions for medical and veterinary use, said compositions having properties of full and effective prevention of and treatment of various inflammations, infections and diarrhoea, while being safe for the environment and the organism (human or animal).

The substances that constitute the essential ingredient of said pharmaceutical compositions which are one of the objects of the present inventions are herbal essences with high contents in thymol, carvacrol and tannin.

These substances can all be obtained from herbs like *Thymus vulgaris, thymus serpilum, saturea hortensis, saturea montana, saturea subricata, carum coptimum*(India), *thymus zygus* (Spain), *ocimum gratisum* (Southern France and Africa), *moranda puntata* (North America), *mosia japanoica maxinowisz* (Japan), *salvia officiaiatis* and the like.

Herbs of the Labiatae family, which have been widely used as spices for flavouring dishes and beverages, are known to contain high amounts of thymol and carvacrol. The most common among them, thyme and oregano, differ from each other mainly in the content ratio of thymol and carvacrol. The essential oil obtained from thyme, which is known to possess antifungal and antimicrobial activity, has a higher content in thymol; on the contrary, herbs of the genus origanum contain predominantly carvacrol.

It was found that thymol alone as well as essential oils containing thymol in amounts corresponding to a carvacrol:thymol ratio of lower than 5:1, which show some antimicrobial activity on certain microorganisms, in particular *Rhizobium legumirosarum*, have the disadvantages that they have mediocre activities on strains of *Staphylococcus aureus* and an inferior activity on *Bacillus subtilis*.

Further, isolated thymol showed a good antimicrobial activity on *Escherichia coli*, while essential oils and their mixtures containing relatively low levels of carvacrol (having a carvacrol:thymol ratio lower than 5:1) resulted in a significantly reduced activity on the same microorganism, leading to the assumption that an antagonistic effect between the other ingredients of the essential oils may affect their activity on *E. coli*.

On the contrary, carvacrol alone, which had a significant antimicrobial activity on *Staphylococcus aureus*, had an inferior activity on *Escherichia coli, Bacillus subtilis* and *Salmonella typi*.

There is thus a continuing need of herbal based pharmaceutical compositions which overcome the above mentioned drawbacks.

SUMMARY OF THE INVENTION

The herbal essential oil contained in the pharmaceutical composition of the present invention is characterised in that the total amount of thymol and carvacrol comprised therein is at least 55%, preferably 70% by weight and in that the ratio of carvacrol to thymol is at least 10:1.

The above given ratio of carvacrol to thymol is found to provide surprising antimicrobial properties, when compared to the corresponding properties of essential oils having a ratio lower than 10:1 and of isolated thymol and carvacrol.

A high total content of thymol and carvacrol in the essential oils is of great significance. When they are contained in the herbs in high amounts, they can be obtained from the leaves and flowers of the herbs by means of simple processes in higher yields. It is therefore possible and preferable to obtain the essential ingredients by a process as simple as steam distillation, which reduces costs at a considerable extent.

Moreover, a high concentration in the essential ingredients has the economical advantage that the essential oil may be used in small quantities to obtain the desirable effects.

Well-balanced overall results were obtained by essential oils having a ratio of carvacrol to thymol in a range of 30:1 to 150:1. The best antimicrobial activities have been observed in the range of 40:1 to 110:1.

A further advantage in the use of the essential oils according to the invention in comparison to the use of isolated carvacrol is the fact that the former are obtainable by simple processes, whereas the isolation of pure carvacrol requires at least an additional chromatographic separation.

Antimicrobial tests were performed on standard microorganisms including *E.coli, Staphylococcus aureus, Salmonella typhi, Rhizobium leguminosarum, Bacillus subtilis* and of the Eimeria group.

The high levels of thymol and carvacrol required by the present invention are obtainable by steam distillation of carvacrol-rich herbs belonging preferably to the genus origanum. The essential oils obtained have a total amount of thymol and carvacrol comprised therein is at least 55%; most of the specimen examined had a total amount in a range between 70 and 88% by weight and a carvacrol to thymol ratio of 40:1 to 110:1 (see Table 1).

*Origanum vulgare* ssp. *hirtum* (a wild growing subspecies of *Origanum vulgare*, growing in the Greek mainland) and *Origanum heracleoticum* (which grows on the island of Crete) are preferred because they contain thymol and carvacrol in levels of higher than 55%, that is much higher than the herbs listed in the introduction above can provide.

The origin of the herbs used may account for the differences in the compositions of the essential oils obtained. Referring to Table 1, it may be generally concluded that the carvacrol predominance is more recognisable in herbs growing in Crete, and that the higher absolute thymol levels are measured in essential oils originating from the island of Euboea. The differences in the compositions may depend on the climatic conditions and their variations.

The essencial oils necessary for the performance of the present invention are preferably obtained from origanum hyrtum and origanum heracleoticum by steam distillation. To do so, the leaves and flowers of the herb, after being dessicated, are firstly charged in an extractor equipped with two tubes for steam and oil passage respectively.

The water vessel positioned below the dessicated herbal leaves and flowers is heated at 100° C. under pressure of 20 kp/cm². The water steam, upon contacting with the dessicated herbs, extracts the essence which is collected and flows from the bottom of the extractor towards a product vessel. This process takes about 3 hours, yielding 5–6 kg of herbal oil (essence) per 100 kg of dessicated herbs.

Following this first distillation step, the herbs are reextracted in the same extractor, replacing the water by a water-alcohol mixture (20% water-80% alcohol), which is again heated at 100° C. This is the second distillation step.

The liquid collected in the product vessel from the bottom of the extractor at the end of the second distillation step is the starting material from which tannin is obtained as follows: The content of the vessel is heated at 80° C. to evaporate the alcohol. After about one hour, the alcohol has fully evaporated and the residue comprises tannin.

The product obtained from the above described steam distillation was subjected to gas chromatography-mass spectroscopy and the analytical results are shown in Table 1.

A commercially available origanum oil was analysed as well, for comparison. It is noted that the origanum oil, which is obtained by cultivated oregano herbs, contains very low levels of carvacrol, being untypical for origanum, but high levels of its precursor γ-terpinene (40 wt %) and significant amounts of camphene (5.4 wt %), limonene (4.1 wt %), α-pinene and α-terpineol.

TABLE 1

| Specimen | Essential oil | Carvacrol (C) | Thymol (T) | Total (C + T) | Ratio (C/T) |
|---|---|---|---|---|---|
| 1 | *Origanum vulgare* ssp. *hirtum* | 83.3 | 1.1 | 84.4 | 75.7 |
| 2 | *Origanum hyrtum* | 79.6 | 2.5 | 82.1 | 31.8 |
| 3 | *Origanum hyrtum* | 72.0 | 1.2 | 73.2 | 60.0 |
| 4 | *Origanum heracleoticum* | 85.3 | 0.9 | 86.2 | 94.8 |
| 5 | *Origanum heracleoticum* | 84.4 | 0.6 | 85.0 | 140.7 |
| 6 | *Origanum heracleoticum* | 82.2 | 0.8 | 83.0 | 102.8 |
| Comparison | *Origanum oil* (commerical) | 0.4 | 31.8 | 32.2 | <1 |

Measurements of antimicrobial activities were carried out using the essential oils as obtained by steam distillation, as well as mixtures of said oils and mixtures of *Origanum vulgare* ssp. *hirtum* oil with *Origanumdictamnus oil* (wild growing in Crete) which has a carvacrol and thymol content of 62.4% and 0.4% respectively (carvacrol to thymol ratio= 152). As mentioned above, good activities were measured at carvacrol:thymol ratios of 30:1 to 150:1 and the best results are obtained in the respective ratio within the range of 40:1 to 110:1 by weight.

It is noted that since carvacrol and thymol are isomeric compounds, their weight ratio corresponds to their molar ratio.

Though it was established that neither γ-terpinene nor p-cymene, the precursors of carvacrol and thymol (which are comprised in the essential oils comprised in the pharmaceutical composition of the invention in levels of 2 to 11% by weight) had any antimicrobial activity, their presence may contribute to the synergistic effect observed with the pharmaceutical composition according to the invention.

According to one aspect of the present invention, there is provided a substitute for antibiotics to be regularly administered on a daily basis to poultry, in order to prevent diarrhoea and coccidiosis.

In another aspect of the present invention, the pharmaceutical composition can be successfully used for the prevention and treatment of coccidiosis, a contagious infection of poultry affecting the intestinal epithelium and causing enteritis and diarrhoea.

In a further embodiment these pharmaceutical compositions are used for the treatment of the following:
 a. chronic mastitis or mastitis caused by Staphylococcus or Streptococcus,
 b. dermal fungal infections and inflammations including infections and inflammations in vagina and/or uterus (humans and animals),
 c. aural infections,
 d. ophthalmic inflammations,
 e. inflammations of lungs (pneumonia), and
 f. inflammations of kidneys (nephritis).

The bactericidal and bacteriostatic activity of the essential oils of the invention was also examined in high dilutions. High bactericidal activities (on *Staphylococcus aureus*) at dilutions of 1:4000 were established, while the bacterial growth rate of the same microorganism was considerably decreased at dilutions of 1:10000 and even 1:50000.

Accordingly, in a preferred embodiment of the present invention, the pharmaceutical composition is used for the purification of water. In a concentration of about 10 to 20 ml of a 5% aqueous solution of the essential oil per cubic meter water, the ingredients of the essential oils according to the present invention provide a bacteriostatic effect without impairing the odour and taste of drinking water. They can therefore be applied as a substitute for chlorine, which is still widely used by municipal water suppliers at levels which are not only questionable with respect to corrosion of the water supplying pipeline but also impart a disagreeable odour to drinking water.

In a further preferred embodiment the pharmaceutical composition of the invention comprises, in addition to the essential oils obtainable by steam distillation, the aqueous alcoholic extract of herbs belonging to the genus Origanum. This extract, which essentially consists of tannin and is obtained by the extraction of the distillation residues as described above, is preferably gained from *Origanum vulgare* ssp. *hirtum* and/or *Origanum heracleoticum*.

The resulting pharmaceutical composition comprising a mixture of the essential oils with the tannin is used in the treatment of diseases caused by pathogenic micro-organisms of the abdominal region. The diseases which may be treated by the pharmaceutical composition of this embodiment are caused by micro-organisms selected from salmonella, staphylococcus, pasteurella and *Escherichia cola*.

The following non limiting examples illustrate the invention. The percentages given represent weight percentages.

EXAMPLES 1 to 9

Examples 1 to 9 concern the preparation of pharmaceutical compositions comprising the essential oil of *Origanum vulgare* ssp. *hirtum* referred to above as Specimen 1.

Example 1

There is provided a pharmaceutical composition for medical and veterinary uses for the treatment of Salmonellasis, Staphylococciasis, Pasteuridiosis and Colabacillosis (caused by *E.coli*) that attack the abdominal region (stomach and intestines) of humans and animals.

The composition is prepared in powder form, in syrup form or in paste form.

| Ingredient | Veterinary use | Medical (human) use |
|---|---|---|
| CaCO$_3$ | 94% | — |
| Lactose | — | 91% |
| Tannin | 1% | 8% |
| *Origanum vulgare* ssp. *hirtum* | 5% | 8% |

The preparation is carried out in a vacuum mixer, where 50 wt % of the total quantity of tannin and oregano essential oil are added to CaCO$_3$ or lactose (depending on the desired use (for human or animal) and the blend is mixed at 200 rpm for 20 minutes. Subsequently the rest of the tannin and oil are added to the blend and are mixed for an additional 45 minutes.

The powder thus produced is packed in packets of 100, 250, 500, 1000, 2000 g, made of plastic layered aluminum foil and in sacks of 25 or 50 kg for the powder intended for veterinary use, while the powder for medical use is filled in 500 mg capsules.

b) Syrup Form

As mentioned above, the pharmaceutical composition for the treatment of Salmonellasis, Staphylococciasis, Pasteuridiosis and Colabacillosis (caused by *E.coli*) can also be in syrup form. The essential starting materials and corresponding amounts for the preparation of said syrups are as follows:

| Ingredient | Veterinary use | Medical (human) use |
|---|---|---|
| Polyethylene glycol | 92.5% | 94.5% |
| *Origanum vulgare* ssp. *hirtum* | 5% | 3% |
| Tannin | 1% | 1% |
| Glycerine monostearate | 1.5% | 1.5% |

The process for preparing the above syrup is carried out in a colloidal mixer, where the polyethylene glycol is charged first and heated at 55° C. for 5 minutes. Subsequently, the *Origanum vulgare* ssp. *hirtum* oil, the tannin and the glycerine monostearate are added and mixed together at the same temperature for 15 minutes at a speed of 300 rpm. The mixture is allowed to cool for one hour and then is mixed again, without heating, for 30 minutes at 300 rpm.

The syrup thus prepared is filled in dark coloured glass flasks of 120 ml and the flasks intended for animal use are provided with a suitable fitter to facilitate administration to animals.

c) Paste Form

According to the same method, but with slight variation of the levels of the various ingredients, a paste form is produced, intended for veterinary use only.

| Ingredients | |
|---|---|
| Polyethylene glycol | 74% |
| *Origanum vulgare* ssp. *hirtum* | 5% |
| Tannin | 1% |
| Glycerine monostearate | 20% |

The paste in filled in 100 ml tubes that are provided with a special nozzle for administration to animals.

Example 2

One additional form of powder is that intended for the prevention and treatment of coccidiosis in poultry, caused by the germs of the Eimeria group (*E. tenella, E. acervulina, E. colhici, E. duodenalis, E. mitri, E. fasiani* and the like). For the preparation of this powder the essential ingradients are used in the following levels:

| Ingredient | Veterinary use (poultry) |
|---|---|
| CaCO$_3$ | 90% |
| *Origanum vulgare* ssp. *hirtum* | 5% |
| Glycerine monostearate | 1% |

The preparation process is the same as above with the difference that tannin is not used.

For the prevention and treatment of coccidiosis, a solution form can also be prepared, with the following essential ingredients in the corresponding levels:

| Ingredients | |
| --- | --- |
| *Origanum vulgare* ssp. *hirtum* | 5% |
| Emulgator 484 | 3% |
| Propylene glycol | 10% |
| Distilled water | 82% |

The preparation is carried out in a colloidal mixer, where the Emulgator 484 is charged first and the essential oil is added and mixed at 200 rpm for 10 minutes. Next, the propylene glycol is added and mixed for an additional 10 minutes and finally the water is added and mixed at the same speed for an additional 10 minutes. The solution thus prepared is filled in 1 liter bottles and is useful in the treatment of coccidiosis in poultry.

The same solution is useful for the purification and disinfection of drinking water. The quantities which provide sufficient bacteriostatic activity without imparting a disagreeable odour are in the range of 10 to 20 ml of the above solution per cubic meter water.

Example 3

Among the pharmaceutical compositions of the present invention, one is intended for the fungal infections of the human and animal skin. The composition may be in the form of tincture or ointment.

a) Tincture form

| Ingredient | Veterinary use | Medical (human) use |
| --- | --- | --- |
| *Paraffinum liquidum* | 95% | — |
| Propylene glycol | — | 95% |
| *Origanum vulgare* ssp. *hirtum* | 5% | 5% |

Depending on the desired end use, propylene glycol or paraffinum liquidum is heated in a vacuum mixer at 55° C. and, at the same temperature, the *Origanum vulgare* ssp. *hirtum* oil is added and mixed for 20 minutes at 450 rpm.

The composition is filled in 10 ml dark coloured vials provided with suitable plastic applicator for skin administration.

b) Ointment Form

For the treatment of dermal fungal infections, the ointment form of the present invention has the following composition:

| Ingredient | Veterinary use | Medical (human) use |
| --- | --- | --- |
| *Paraffinum liquidum* | 25% | 20% |
| *Origanum vulgare* ssp. *hirtum* | 5% | 5% |
| *Vaselinum album* | 70% | 75% |

The preparation takes place in a colloidal mixer, where the paraffinum liquidum is charged first and heated at 55° C. Next, the origanum oil is added and mixed for 15 minutes at 300 rpm. Vaseline is preheated at 65° C. and then added to the mixture. The total is mixed for 45 minutes at 600 rpm. Before the mixture is cooled, it is charged in a suitable funnel for filling tubes.

Example 4

For the treatment of breast inflammations in animals (mastitis caused by Staphylococcus, Streptococcus as well as chronic mastitis) there is a process for the preparation of a composition comprising the following ingredients:

| Ingredients | |
| --- | --- |
| *Paraffinum liquidum* | 45% |
| *Origanum vulgare* ssp. *hirtum* | 5% |
| *Vaselinum album* | 50% |

The process comprises heating the paraffinum liquidum at 55° C. in a colloidal mixer, where the *Origanum vulgare* ssp. *hirtum* oil is subsequently added and mixed for 15 minutes at 300 rpm. The vaseline, preheated at 65° C., is introduced to the mixture and the total is mixed for 45 minutes at 600 rpm.

The mixture, as it is, is filled in 10 ml plastic syringes fitted with stopper and suitable nozzle for administration to the breast duct.

Example 5

For the treatment of infections and inflammations caused by various germs and fungi in the vagina and uterus of women and female animals, there is a process for the preparation of a composition in the form of vaginal suppositories comprising the following ingredients:

| Ingredients | |
| --- | --- |
| *Origanum vulgare* ssp. *hirtum* | 3% |
| Hygroscopic carrier | 97% |

The process comprises mixing in a colloidal mixer, without heating, the *Origanum vulgare* ssp. *hirtum* oil and the hygroscopic carrier for 30 minutes at 300 rpm. In the same vat, the mixture is placed in a suppository forming press, which forms suppositories by pressing the mixture in heated moulds. The produced suppositories of 5, 10 or 20 g are packed in airtight package.

Example 6

For the treatment of aural infections including otitis caused by various germs in humans and animals, there is a process for the preparation of a composition in the form of drops comprising the following ingredients:

| Ingredients | |
| --- | --- |
| *Origanum vulgare* ssp. *hirtum* | 3% |
| *Paraffinum liquidum* | 97% |

The process comprises heating in a colloidal mixer the paraffinum liquidum at 55° C., adding the *Origanum vulgare* ssp. *hirtum* oil and mixing the blend for 20 minutes at 300 rpm. The product is filled in dark coloured vials with suitable dropper tube.

Example 7

A pharmaceutical composition for the treatment of inflammations caused by various germs in injuries of humans and animals, is in the form of spray or powder.

a) Powder Form

For the powder form, the ingredients are used in the following amounts:

| Ingredients | Veterinary use | Medical (human) use |
|---|---|---|
| *Origanum vulgare* ssp. *hirtum* | 3% | 5% |
| Starch | 97% | — |
| Baby powder Neutral | — | 95% |

Equal quantities of powder (starch or baby powder Neutral, according to the end use) and *Origanum vulgare* ssp. *hirtum* oil are charged in a vacuum blender and blended for 10 minutes at 60 rpm. Then half of the remaining powder is added and blended for 20 minutes at the same speed. Finally, the remaining powder is added and blended at 300 rpm for 30 minutes. The powder obtained is filled in plastic layered aluminum bags of 100 g.

b) Spray Form

In order to prepare the spray form for veterinary use only the ingredients listed below are used in the following amounts:

| Ingredients | |
|---|---|
| *Origanum vulgare* ssp. *hirtum* | 3% |
| Carrier | 97% |

The total quantities of the ingredients are mixed in a colloidal mixer at 600 rpm for 30 minutes and the blend is filled in 200 ml flasks equipped with a suitable spraying pump.

Example 8

A pharmaceutical composition directed to the treatment of inflammations of the lungs and kidneys of animals (pneumonia, nephritis) is in form of an injectable solution for intramuscular administration to animals, comprising the following ingredients:

| ingredients | |
|---|---|
| *Origanum vulgare* ssp. *hirtum* | 1.5% |
| Polyethylene glycol | 98.5% |

Polyethylene glycol is heated in a colloidal mixer at 55° C., the origanum hyrtum oil is added to the mixer and the total is mixed at 600 rpm for 30 minutes. The solution is filled in 120 ml airtight flasks fitted with a suitable rubber stopper.

Example 9

Another application is a pharmaceutical composition for the treatment of ophthalmic inflammations that cause conjunctivitis in humans and animals, comprising the following components:

| Ingredients | Veterinary use | Medical (human) use |
|---|---|---|
| *Paraffinum liquidum* | 37% | — |
| *Origanum vulgare* ssp. *hirtum* | 3% | 2% |
| *Vaselinum album* | 60% | 98% |

The process is carried out in a colloidal mixer, where vaseline preheated to 65° C. is charged followed by the remaining ingredients. The blend is mixed at 300 rpm for 30 minutes. The product is packed in tubes of 100 and 20 g, depending on the desired use (veterinary or medical).

Pharmaceutical compositions may be prepared by application of the same methods and using the same ingredients as described in Examples 1 to 9 except for the substitution of *Origanum vulgare* ssp. *hirtum* by *Origanum heracleoticum* (referred to above as Specimen 4) as well as by any of the other specimens of Table 1.

A mixture of the essential oils of *Origanum vulgare* ssp. *hirtum* (Specimen 2) and *Origanum heracleoticum* (Specimen 5) (as obtained by steam distillation) in a 1:1 weight ratio, comprising carvacrol and thymol in levels of 82.0% and 1.5% respectively (carvacrol:thymol ratio=54, 7:1), may also be used in the same amounts as *Origanum vulgare* ssp. *hirtum* oil in Examples 1 to 9 for the preparation of the analogous pharmaceutical compositions.

I claim:

1. An antimicrobial pharmaceutical composition comprising an antimicrobial-effective amount of an essential oil obtained from *Origanum vulgare* ssp. *hirtum* containing thymol and carvacrol as its main ingredients, and a pharmaceutically acceptable carrier, wherein
   (a) the total amount of thymol and carvacrol in said essential oil is at least 55%, by weight, of said essential oil, and
   (b) the ratio of carvacrol to thymol is at least 10:1.

2. The pharmaceutical composition according to claim 1, wherein said ratio of carvacrol to thymol is in the range of 30:1 to 150:1 and said essential oil is obtained by steam distillation of said *Origanum vulgare* ssp. *hirtum*.

3. The pharmaceutical composition according to claim 1, wherein said essential oil is obtained by aqueous alcoholic extraction of said *Origanum vulgare* ssp. *hirtum*.

4. The pharmaceutical composition according to claim 3 for use in the treatment of diseases caused by pathogenic microorganisms of the abdominal tract.

5. The pharmaceutical composition according to claim 1 for use in the prevention and treatment of coccidiosis in poultry.

6. The pharmaceutical composition according to claim 1 for use in the treatment of diseases selected from the group consisting of:
   a) chronic mastitis or mastitis caused by Staphylococcus or Streptococcus,
   b) dermal fungal infections and inflammations including infections and inflammations in a vagina or uterus,
   c) aural infections,
   d) ophthalmic inflammations,
   e) inflammations of lungs or pneumonia, and
   f) inflammations of kidneys or nephritis.

7. The pharmaceutical composition according to claim 1 for use in disinfecting water.

8. The composition according to claim 1, wherein the total amount of thymol and carvacrol in said essential oil is at least 70%, by weight, of said essential oil.

9. A method of preparing an antimicrobial pharmaceutical composition comprising obtaining the essential oil of *Origanum vulgare* ssp. *hirtum* by steam distillation and mixing an antimicrobial-effective amount of said essential oil with a pharmaceutically acceptable carrier, wherein (a) the total amount of thymol and carvacrol in said essential oil is at least 55%, by weight, of said essential oil, and (b) the ratio of carvacrol to thymol is at least 10:1.

10. The method according to claim 9, wherein said ratio of carvacrol to thymol in said essential oil is in the range of 30:1 to 150:1.

11. The method according to claim 9, further comprising obtaining the essential oil of *Origanum vulgare* ssp. *hirtum* by aqueous alcoholic extraction and admixing it with the essential oil obtained by steam distillation and the pharmaceutically acceptable carrier.

12. A method of treating or preventing coccidiosis in poultry comprising the step of administering to poultry an effective amount of the anitmicrobial pharmaceutical composition according to claim 9.

* * * * *